US 6,696,078 B1

(12) United States Patent
Masters

(10) Patent No.: US 6,696,078 B1
(45) Date of Patent: Feb. 24, 2004

(54) SYSTEM AND METHODS FOR LOCAL INTRADERMAL TREATMENT

(76) Inventor: Edwin J. Masters, 325 Kennedy, Sikeston, MO (US) 63801

( * ) Notice: Subject to any disclaimer, the term of this patent is extended or adjusted under 35 U.S.C. 154(b) by 0 days.

(21) Appl. No.: 09/359,344

(22) Filed: Jul. 21, 1999

(51) Int. Cl.[7] .................. A61F 13/00; A61F 13/02; A61L 15/16
(52) U.S. Cl. .................. 424/449; 424/443; 424/448
(58) Field of Search ................ 514/353, 280; 424/449

(56) References Cited

U.S. PATENT DOCUMENTS

| | | | | |
|---|---|---|---|---|
| 4,767,750 A | * | 8/1988 | Jacquet et al. | |
| 4,895,727 A | * | 1/1990 | Allen | |
| 5,240,917 A | | 8/1993 | Keimowitz et al. | |
| 5,414,014 A | * | 5/1995 | Schneider et al. | 514/535 |
| 5,460,620 A | * | 10/1995 | Smith et al. | |
| 5,543,417 A | * | 8/1996 | Waldstreicher | |
| 5,700,457 A | * | 12/1997 | Dixon | 424/78.02 |
| 5,725,875 A | * | 3/1998 | Noll et al. | |
| 5,886,003 A | * | 3/1999 | Cohen et al. | 514/280 |
| 5,994,372 A | * | 11/1999 | Yaksh | |
| 6,333,356 B1 | * | 12/2001 | Ptchelintsev et al. | |

* cited by examiner

Primary Examiner—Thurman K. Page
Assistant Examiner—Isis Ghali
(74) Attorney, Agent, or Firm—Armstrong Teasdale LLP

(57) ABSTRACT

A system and methods for local intradermal treatment of a dermal injury carrying the risk of innoculation with an identified pathogen or pathogens carried by an identified vector is described. In one embodiment, the system includes a multidrug pharmaceutical composition specifically targeting the pathogen or pathogens known to be carried by the identified vector. The pharmaceutical composition is applied to a dermal patch, which is applied to the skin at the site of dermal injury. The pharmaceutical composition further includes an enhancer for facilitating the penetration and absorption of the pharmaceutical composition into the dermal layers. The pharmaceutical composition provides local, intradermal drug concentrations which are sufficient to substantially eradicate or inhibit a pathogen while it remains intradermally localized.

10 Claims, 1 Drawing Sheet

SYSTEM AND METHODS FOR LOCAL INTRADERMAL TREATMENT

BACKGROUND OF THE INVENTION

This invention relates generally to systems and methods of dermal drug and chemical delivery, and more particularly, to a system and methods for local intradermal prophylaxis and treatment of pathogens introduced by dermal injury from a known vector.

Many disease causing agents, including bacteria, viruses, protozoans, toxins and venoms, are introduced by innoculation into or through the skin, for example by dermal injuries such as insect, spider or snake bites, other skin punctures such as needle sticks, or through abrasions. During the initial stage of infection or envenomation, many of these agents remain localized in an area within centimeters of the initial innoculation site, and only later begin to affect the body systemically. A classic example is Lyme borreliosis, commonly known as Lyme disease, produced by a tick-borne spirochete. The typical clinical course of the disease begins with innoculation through the bite of an infected tick, followed by the appearance of the distinctive, "bulls-eye" erythema migrans rash at the site of innoculation. It is believed that the spirochete initially remains localized in the skin for a period of days before multiplying to establish infection.

In later stages of infection the spirochetes disseminate and can be found in remote skin sites, blood, cerebrospinal fluid, synovial fluid, and other tissues. Later stage Lyme disease symptoms include joint swelling and arthritis; carditis; memory loss, localized paralysis, paresthesias and other symptoms of CNS involvement; and nonspecific symptoms such as fatigue. Once this stage of infection has been reached, eradication of the spirochete and elimination of Lyme disease symptoms can prove frustratingly difficult. Systemic administration of antibiotic is the standard treatment, but even with aggressive, systemic antibiotic treatment during the early stage of the disease, the treatment failure rate for documented Lyme disease can be as high as 10%. Still, general agreement exists that the earlier and more aggressive the treatment, the better the patient outcome.

However, aggressive treatment at the earliest stage possible, that is immediately after a feeding tick has been spotted and removed, is controversial. Many health care workers question the advisability of oral systemic, prophylactic antibiotic therapy for tick bites, which entails days or weeks of exposure to systemic antibiotics. The cost and side effects associated with so treating the enormous number of tick bites incurred each year must be weighed against the relatively small chance of actual disease transmission of an admittedly serious illness. The treatment controversy is further complicated by the fact that some other tick-vectored illnesses, particularly Rocky Mountain Spotted Fever and Ehrlichiosis, can and do kill otherwise healthy individuals, especially children. A premium therefore exists on finding a way to safely and effectively treat such infections at the earliest possible stage.

Like Lyme borreliosis, many other diseases follow a similar pattern of localized innoculation followed by later systemic infection. These include the other tick-vectored illnesses such as Q-fever, Babesiosis, Tularemia, and relapsing fevers, as well as Rocky Mountain Spotted Fever and Ehrlichiosis. Malarial infection by mosquito vectors follows a similar pattern, as do envenomations from bites of arthropods such as the brown recluse spider. Needlestick injuries also carry the risk of hepatitis-B, syphilis, HIV and other infections following the same pattern of initially localized infection, with devastating later stage systemic effects. As with the treatment of Lyme borreliosis, the chances of treatment success for all of these illnesses are greatly enhanced by catching and treating the infection or envenomation at the site of innoculation before systemic dissemination of the pathogen or toxin. Further, because some of these pathogens are known to remain viable in stored blood for up to about two weeks, early treatment and eradication of pathogens before they invade the circulatory system would improve the safety of the blood supply.

The known treatments for such infections or envenomations after localized innoculation consist of an aggressive course of antibiotic or antiviral medication administered systemically. Depending on the pathogen involved and the timing of the treatment relative to the moment of innoculation, such treatments can have a high success rate. However, high systemic doses of antibiotics or antivirals frequently have side effects such as allergic reactions, severe gastrointestinal disturbance, ototoxicity, renal toxicity, pericarditis, etc. The risk of such side effects is particularly vexing in combination with the need for early and aggressive treatment in order to reduce the risk of treatment failure. Furthermore, at least in the case of the Lyme disease spirochete, aggressive systemic antibiotic treatment does not preclude survival of viable bacteria in sequestration.

Transdermal drug delivery systems are known. With such systems are used to infuse drugs systemically at a stable rate over an extended period of time of hours or days. These infusion systems, typically in the form of patches, are used, for example, to deliver compositions containing a single systemically acting drug such as nicotine, nitroglycerin, estradiol, or scopolamine. However, the use of intradermal, local drug delivery for prophylactic and local treatment of infections resulting from innoculations such as bites or needle-sticks is not known.

It would therefore be desirable to provide systems and methods for local, intradermal prophylaxis and treatment of innoculations. It would also be desirable to provide systems and methods which treat innoculations at the earliest stages of potential infection or envenomation. It would be further desirable to provide such systems and methods which are targeted against specific vectors. It would be still further desirable to provide such systems and methods including both early and later, ongoing treatment of innoculations. It would be yet still further desirable to provide such systems and methods which are simple to use for non-medically trained individuals.

BRIEF SUMMARY OF THE INVENTION

In an exemplary embodiment, a system and methods for local intradermal treatment of pathogens includes a vector-specific pharmaceutical composition including drugs or chemicals, or combinations thereof, specifically targeted against a pathogen or pathogens, including bacteria, viruses, toxins, protozoa and venoms known to be carried or potentially carried by the identified vector. The pharmaceutical composition is applied to an area of skin surrounding the site of a dermal injury inflicted by the known vector, the dermal injury thus carrying the risk of innoculation with a pathogen or pathogens from the identified vector. For example, such dermal injuries include insect, snake and arthropod bites, accidental needlesticks, and abrasions. The pharmaceutical composition includes a drug, multidrug, chemical or multichemical combination, plus an enhancer or enhancers for facilitating the penetration and absorption of the pharmaceutical composition into the dermal layers at the site of dermal injury. More specifically, and in one aspect, the pharmaceutical composition provides local, intradermal drug concentrations which are sufficient to substantially eradicate or inhibit a pathogen while it remains localized.

The local intradermal system and methods provide intradermal prophylaxis and treatment of innoculations during the early, localized stages of infection or envenomation. In addition, the system and methods can provide later, ongoing treatment against any surviving pathogens. Further, the local intradermal system and methods are targeted against specific, readily identifiable vectors and their associated pathogens, and are simple to use for non-medically trained individuals. Still further, the system and methods are compact, lightweight and easily packed in gear such as camping gear, emergency gear and the like.

DETAILED DESCRIPTION OF THE INVENTION

Figure 1:
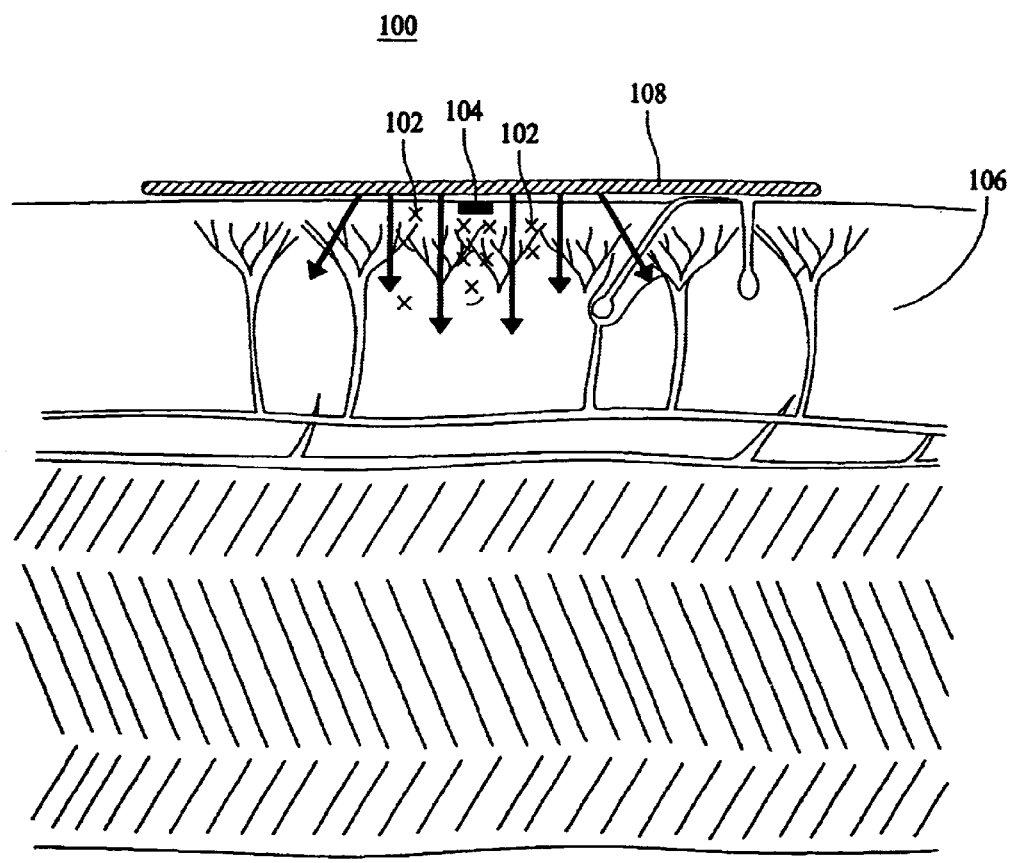
FIG. 1 is a schematic illustration of a system and method for local intradermal prophylactic treatment of a dermal injury resulting in innoculation of a pathogen.

FIG. 1 is a schematic illustration of an exemplary embodiment of a system 100 and method for local, intradermal prophylactic treatment of a pathogen 102 introduced by innoculation following a dermal injury 104 to skin 106. As used herein, the term dermal injury refers to any dermal injury inflicted by a known pathogen vector, and thus carrying a risk of innoculation with a known pathogen or pathogens associated with the vector. Such dermal injuries include, but are not limited to, insect, snake and arthropod bites, needlesticks, abrasions and other skin wounds. Further, as used herein, the term pathogen refers to any disease causing agent including a microorgansim such as a bacterium, virus or protozoan, any living organism such as a parasite, or any toxin or venom. Still further, as used herein, the term drug or drugs refers to any pharmaceutically active agent including drugs and chemicals having an effect on identified pathogens, including microorganisms, parasitic organisms, toxins and venoms.

In the one embodiment, system 100 includes a dermal patch 108, to which a pharmaceutical composition (not shown) is applied. The pharmaceutical composition includes a single drug or chemical, or a combination of drugs or chemicals targeted against a specific pathogen orpathogens potentially introduced by a specific vector, plus an enhancer or enhancers for facilitating the penetration and absorption of the pharmaceutical composition into the dermal layers. More specifically, and in one aspect, the pharmaceutical composition is formulated to provide local, intradermal concentrations of the active drugs or chemicals which are sufficiently high to eradicate, nearly eradicate, or inhibit the pathogen within the period that it remains intradermally localized. In another aspect, the system and methods are useful for both local prophylactic treatment immediately after a dermal injury carrying a risk of innoculation with an identified pathogen or pathogens has been identified, and later, ongoing treatment for any persisting localized infection or tissue injury, including treatment of symptoms such as pain or itching, and treatment of opportunistic infections.

In one embodiment, patch 108 is fabricated of plastic material such as that commonly used for transdermal patches for systemic infusion of the drugs nicotine and nitroglycerin, for example. The pharmaceutical composition is applied to one surface of patch 108, adhesive applied to the same surface, and the surface covered with a peel-away backing. Patch 108 is then individually packaged in a paper, plastic or foil packet, ready to be stored for later use. Each packet identifies the indications for use of patch 108, for example by identifying the vector and pathogen for which patch 108 is used. In one embodiment, multiple patches 108, each having a different pharmaceutical composition targeted against different vectors and associated pathogens, are made available. Once an individual sustains a bite or other type of dermal injury carrying a risk of innoculation, the vector and pathogen or pathogens are identified and the vector specific patch 108 selected and applied as soon as possible to the innoculation site.

By changing the pharmaceutical composition, the system and methods can be used to treat a wide range of pathogens introduced by innoculations from different vectors. For example, the system and methods can be used for treating pathogens introduced by insect bites, accidental needlesticks, and venoms or toxins or other pathogens introduced from the bites of venomous or infectious arthropods and reptiles, or any pathogen introduced by innoculation through or into the skin. Thus, depending on the vector, associated risk of infection or envenomation, and associated symptoms, the specifically targeted pharmaceutical composition includes active drugs or chemicals chosen from several categories including, but not limited to, the following: antibiotics, antivirals, antipruritics, antihistamines, anti-inflammatories, antitoxins, antivenoms, vasoconstrictors to slow blood flow and retard dissemination of the pathogen from the innoculation site, steroids to minimize adverse dermal reactions, antibodies plus complement to inhibit the pathogen, and local anaesthetics such as lidocaine or benzocaine and topical analgesics for pain or itching,. The exact combination of active drugs or chemical in the pharmaceutical composition depends on the targeted vector and associated pathogen or pathogens.

The pharmaceutical composition further includes an absorption or penetration enhancer or enhancers chosen to result in a predetermined rate of delivery of the chosen active drugs or chemicals in the pharmaceutical composition. Suitable absorption enhancers include, for example, dimethyl sulfoxide (DMSO), DMSO-like compounds, ethanolic compounds, pyroglutamic acid esters and other solvents or compounds known to those skilled in the pharmaceutical art which facilitate dermal penetration of the drugs or chemicals chosen for the pharmaceutical composition. The absorption enhancer chosen and the relative proportion of the absorption enhancer with respect to the active drugs or chemicals depends on the desired rate of delivery of the drugs or chemicals into the skin, which in turn depends on the targeted pathogen and time course of infection. More specifically, the type and amount of enhancer is chosen so that a sufficiently high concentration of active drugs or chemicals is attained in the skin to treat the infection within the time period that the particular infection typically remains localized. Generally, the desired rate of delivery is measured in milligrams of active drugs or chemicals infused locally per hour or per day, to reach intradermal concentrations consistent with or exceeding known minimal inhibitory concentrations (MIC's) as known to those skilled in the medical and pharmaceutical arts, depending on the targeted pathogen and the drug or chemical combination used.

In one embodiment, for example, system 100 is used to treat for Lyme borreliosis, commonly known as Lyme disease, and produced by the tick-borne spirochete *Borrelia* burgdorfefi. Classic *B. burgdorferi* infection follows a pattern including an early, localized stage followed by a later, disseminated stage. The early localized stage commonly lasts for days, and subsequent to the bite is most often confirmed by the appearance of the distinctive, "bulls-eye" erythema migrans rash surrounding the site of the bite by an infected tick. During the early localized stage, the spirochetes remain localized in the skin while multiplying to establish the later, disseminated infection. Thus, both the location of an identified tick bite and the appearance of the rash, or either one alone, provide a readily visible indicator for locating the initial, localized site of *B. burgdorferi* infection, or potential infection.

Treatment of *B. burgdorferi* infection at the early, localized stage is important because the later, disseminated stage of Lyme disease produces serious symptoms such as joint swelling and arthritis, carditis, memory loss, localized paralysis, paresthesias and other symptoms of CNS involvement, and nonspecific symptoms such as severe fatigue. Further, once *B. burgdorferi* infection advances past the localized stage and becomes disseminated, eradication of the spirochete is much more difficult and expensive. Thus, the chances of successful treatment and prevention of morbidity and disability are greatly enhanced by catching and treating the infection at the early, localized stage.

Once a feeding tick has been spotted and carefully removed from the skin, the site of innoculation, or potential innoculation, with *B. burgdorjeri* is readily identified by the location of the tick bite. System 100 is then used to treat the bite and catch the potential *B. burgdorferi* infection at the localized stage. In the one embodiment as shown in FIG. 1, the method simply includes the step of applying self-adhesive patch 108 to the skin at the site of the tick bite 104, wherein patch 108 is approximately centered over site 104. In one embodiment, patch 108 is approximately 1 cm to approximately 10 cm in diameter or width, covering an area of skin from about 0.5 $cm^2$ up to about 80 $cm^2$. In one embodiment, patch 108 is circular and has a diameter of about 1 cm to about 5 cm. In another embodiment, patch 108 is circular and has a diameter of about 1 cm. However, the size and shape of patch 108 varies with the type of innoculation and pathogen being targeted, the area of the body where the innoculation is located, the drugs or chemicals included in the pharmaceutical composition, and the timing of treatment relative to the moment of innoculation. Patch 108 is worn continuously for hours or days depending upon the concentration, half-life and efficacy of the drugs or chemicals used to treat the pathogen or toxin. Use of patch 108 to apply the pharmaceutical composition has the advantage of preventing scratching at the innoculation site, thus reducing the chances of scarring and also the chances of introducing an opportunistic infection from, for example, staph or strep bacteria.

In one exemplary embodiment, the pharmaceutical composition for treating *B. burgorferi* infection includes at least two antibiotic drugs, both effective against *B. burgdorferi* but with differing half-lives, one having a relatively short half life and the other a relatively long half-life. The drug with the shorter half-life is used to rapidly provide a high intradermal concentration of antibiotic which is sufficient to eradicate, or nearly eradicate the spirochete. The drug with the longer half-life is used to eradicate any spirochetes which survive to multiply despite the first, shorter-lived antibiotic. One suitable pharmaceutical composition includes, for example, doxycycline and azithromycin. In alternative embodiments, the pharmaceutical composition includes doxycycline with another of the macrolide antibiotics. The absorption enhancer is, for example, a pyroglutamic acid ester. In another alternative embodiment, the pharmaceutical composition for treating a tick bite includes both antibiotics and antivirals, to treat simultaneously for arthropod-borne infections such as encephalitis and bacterial infection.

Local, intradermal administration of doxycycline which lasts for hours or days avoids the known side effects and problems associated with a longer term of systemic administration of doxycycline or other tetracyclines. Such problems include staining of teeth and dentition problems, especially in the very young. Further, the local, intradermal administration of such antibiotics is prophylactic and effective against several tick-vectored illnesses, including the sometimes fatal HME or HGE Ehrlichiosis. Other tick-vectored illnesses which follow a similar pattern of localized infection after innoculation, followed by systemic infection, and can be treated using system 100 include, for example, Rocky Mountain Spotted Fever, Q-fever, Babesiosis, Tularemia, HME or HGE Ehrlichiosis, and relapsing fevers.

For vector-specific, prophylactic treatment against more than one or all of these illnesses, the pharmaceutical composition is varied to include combinations of drugs specifically directed toward the multiple pathogens potentially introduced by the specific tick vector. In one embodiment, the pharmaceutical composition includes a combination of a tetracycline class antibiotic such as doxycycline, plus a macrolide antibiotic such as azithromycin. This combination provides prohylaxis against all six major North American and European, nonviral tick-borne pathogens, including those responsible for Lyme borreliosis, Rocky Mountain Spotted Fever, Tularemia, Babesiosis, and both HME and HGE Ehrlichiosis. Thus, the vector-specificity of the local intradermal prophylactic treatment system and methods means that they are especially suitable for addressing the growing incidence of tick-borne co-infections.

More specifically, in one exemplary embodiment of the pharmaceutical composition targeted against the Ixodes tick which carries the pathogens responsible for causing Lyme borreliosis and HGE Ehrlichiosis, the pharmaceutical composition includes doxycycline, trovafloxacin or a similar drug which treats for both pathogens. Alternatively, the pharmaceutical composition includes a combination of doxycycline and trovafloxacin or a similar drug. In an alternative embodiment which adds prophylaxis against Babesiosis to prohylaxis against Lyme borreliosis and HGE Ehrlichiosis, the pharmaceutical composition includes doxycycline and one of azithromycin, atovaquone and clindamycin, or a combination of any of these last three. In an alternative embodiment for patients allergic to the tetracyclines, the pharmaceutical composition includes trovafloxacin or a similar drug and azithromycin or another macrolide antibiotic. Azithromycin is especially suitable for use in the pharmaceutical compositions because it has a broad antimicrobial spectrum, achieves high tissue concentrations, is generally accepted as very safe, and has a relatively long halflife of several days.

In alternative embodiments, system 100 is used to treat any other pathogen which is commonly introduced through some type of innoculation of a pathogen, which is followed by a first, intradermally localized stage of infection and then a later disseminated stage. Such pathogens include bacteria, viruses, venoms, toxins, protozoa and parasites such as insects or worms. For example, in one embodiment, system 100 is used at the site of a mosquito bite to treat for mosquito-vectored malarial infection caused by protozoa. In such an embodiment, the pharmaceutical composition includes, for example, mefloquin or another antimalarial drug. In alternative embodiments, the antimalarial drug is combined with an antibiotic such as, for example, doxycycline, azithromycin, or a combination thereof. In particular for mosquito bites, the bites may be numerous enough that treatment with dermal patches may not be convenient or practical. In an alternative embodiment especially suitable for such cases, system 100 is implemented as a topically applied cream, ointment or gel including the pharmaceutical composition, as described further below.

In another alternative embodiment, system 100 is used to treat envenomations from bites of arthropods such as the brown recluse spider. For example, in one embodiment to treat a brown recluse spider bite, the pharmaceutical composition includes a specific antivenom plus the penetration or absorption enhancer. In still another alternative embodiment, system 100 is used to treat the bites of poisonous snakes, wherein the pharmaceutical composition includes a combination of drugs chosen to inhibit the action of the venom, inhibit dissemination and reduce inflammation. For example, in one embodiment the pharmaceutical composition to treat a snake bite includes snake antivenom for the particular snake, antibodies plus complement, vasoconstrictors, an anti-inflammatory agent such as hydrocortisone, and the penetration enhancer, or any combination thereof. In alternative embodiments the pharmaceutical composition is varied to include other known drug or chemical therapies against a particular type of snake bite.

In yet still other alternative embodiments, accidental needlesticks known to carry the risk of infection with a virus such as the hepatitis-B virus or HIV, are also treated with system 100, wherein the pharmaceutical composition includes a suitable antiviral drug, drug combination or cocktail. For example, to treat an accidental needlestick with a needle previously used to treat a patient potentially infected with hepatitis-B or HV, the pharmaceutical composition includes one of the antivirls zidovudine, lamivudine, or indinavir, or antinucleic acid agents, or any combination thereof. In one alternative embodiment especially suitable for treating against potential hepatitis B infection, the antiviral lamivudine is included. Needlesticks are also a potential source foraccidental innoculation with the syphilis bacterium. In one embodiment suitable for treating against both the syphilis bacterium and viral infection, a broad spectrum antibiotic such as doxycycline or ceftriaxone, or a combination thereof, is added to a pharmaceutical composition including an antiviral as detailed above.

In alternative embodiments of system 100, the pharmaceutical composition is formulated as a topically applied cream, ointment or gel which is directly applied to the local site of innoculation. The cream, ointment or gel includes the pharmaceutical composition in a suitable solvent or carrier such as, for example, a petrolatum or other oil-based carrier. The cream or ointment is used in areas of hairy skin to which an adhesive patch such as patch 108 does not readily adhere, or used to apply the pharmaceutical composition in cases of involving multiple potential innoculation sites, such as cases of multiple insect bites.

The system and methods for local intradermal treatment of pathogens, venoms or toxins provides a simple and fast way to treat potentially serious infections or envenomations before they progress beyond an early, intradermally localized stage. More specifically, the vector-specific pharmaceutical composition is targeted against specific vector-associated pathogens, toxins or venoms and locally delivers high intradermal concentrations of specific drugs or chemicals at the vector innoculation site. The system and methods act to eradicate or inhibit the pathogen or pathogens, and also to relieve specific symptoms such as pain, itch or swelling which are associated with an innoculation. More specifically, in alternative embodiments the pharmaceutical composition can include a local anaesthetic, antihistamine, antipruritic, steroid, anti-inflammatory, or any combination thereof, for further pain relief and prevention of tissue damage after an innoculation or potential innoculation. Further, the system and methods are simple to practice, and the system in the form of a patch, cream, gel or ointment is compact and easily packed in gear used by military personnel, volunteer workers, campers and other outdoors enthusiasts who are commonly exposed to various disease vectors and venomous animals.

The vector-directed, prophylactic approach of system 100 toward tick-borne co-infections is especially useful because of the tendency for all tick-borne, antibiotic-sensitive pathogens to clinically present with similar non-specific symptoms such as fever, myalgia, weakness, etc. Further, no sensitive and specific diagnostic tests exist to distinguish among infections of the different athogens. Therefore, waiting to diagnose and treat a sick, febrile patient for a single, specific tick-borne pathogen is often frustrating, expensive and inconclusive. The prophylactic systems and methods provide a way to avoid the costs and health problems associated with waiting to treat for a specific pathogen after an identified tick bite.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method for the localized preemption of hyperalgesia and/or treating dermal injury carrying a risk of inoculation with at least one pathogen, the method comprising applying to the dermal injury a dermal patch comprising a mixture of a penetration enhancer, at least one macrolide antibiotic, and at least one tetracycline antibiotic which reduces intradermal levels of the at least one pathogen to inhibit said at least one pathogen while said at least one pathogen remains localized on the dermal area.

2. The method according to claim 1 where said injury is an insect bite, an arthropod bite or a snake bite and wherein the composition is applied in an amount to eradicate or inhibit a pathogen while said at least one pathogen remains localized.

3. The method according to claim 1 wherein the at least one pathogen is at least one microorganism, at least one parasite, at least one toxin or at least one venom.

4. The method according to claim 1 wherein the at least one microorganism is at least one bacterium, at least one virus or at least one protozoan.

5. The method according to claim 1 wherein the at least one pharmaceutically active agent is at least one antibiotic, which reduces intradermal levels of the at least one microorganism.

6. The method according to claim 2 wherein the at least one antibiotic is at least two antibiotics comprising a tetracycline class antibiotic and a macrolide antibiotic.

7. The method according to claim 3 wherein the tetracycline class antibiotic is doxycycline and the macrolide antibiotic is azithromycin.

8. The method according to claim 1 wherein the composition further comprises an antipruritic, a steroid, an anti-inflammatory or a combination thereof.

9. The method according to claim 1 wherein the composition further comprises at least one absorption enhancer.

10. The method according to claim 1 wherein the composition is a dermal patch, a cream, a gel or an ointment.

* * * * *